US007729774B1

(12) United States Patent
Lynch et al.

(10) Patent No.: US 7,729,774 B1
(45) Date of Patent: Jun. 1, 2010

(54) SHELL FOR EXTERNAL COMPONENTS OF HEARING AID SYSTEMS

(75) Inventors: Douglas P Lynch, Valencia, CA (US); Scott A Crawford, Castaic, CA (US)

(73) Assignee: Advanced Bionics, LLC, Valencia, CA (US)

( * ) Notice: Subject to any disclaimer, the term of this patent is extended or adjusted under 35 U.S.C. 154(b) by 1838 days.

(21) Appl. No.: 10/741,411

(22) Filed: Dec. 19, 2003

Related U.S. Application Data

(60) Provisional application No. 60/435,407, filed on Dec. 20, 2002.

(51) Int. Cl.
*A61N 1/00* (2006.01)

(52) U.S. Cl. ........................................................ 607/57

(58) Field of Classification Search ................... 607/55, 607/56, 57

See application file for complete search history.

(56) References Cited

U.S. PATENT DOCUMENTS

D290,511 S 6/1987 Heide
4,831,655 A 5/1989 Buettner
5,183,953 A 2/1993 Anderson et al.
5,249,234 A 9/1993 Butler
5,533,130 A 7/1996 Staton
5,781,637 A 7/1998 Heide et al.
6,105,713 A 8/2000 Brimhall et al.
6,393,130 B1 5/2002 Stonikas et al.
7,003,356 B2 * 2/2006 Tsukamoto et al. ........... 607/57
7,142,926 B2 * 11/2006 Crawford ..................... 607/55

OTHER PUBLICATIONS

Just Bekuz Products Co., "Super Seals(tm) Web site", ((c) 1997; as archived by web.archive.org on Jun. 30, 1998).
Shlafer, M., "Aesthetics—2: Past, Present . . . and Future?", http://www-personal.umich.edu/~mshlafer/hearing3a.html, (created Aug. 1997; updated Aug. 2003).

* cited by examiner

*Primary Examiner*—George R Evanisko
*Assistant Examiner*—Alyssa M Alter
(74) *Attorney, Agent, or Firm*—Mary Elizabeth Bush; Victoria A. Poissant; Bryant R. Gold

(57) ABSTRACT

Detachable shells on hearing system components are used to provide protection to the hearing system components, to be visually pleasing, to provide visibility and to increase system attachment stability, among other functions. The detachable shells allow the overall shape and appearance of the components to be changed, thereby complementing a variety of activities that constitute a hearing system user's unique lifestyle.

20 Claims, 12 Drawing Sheets

SHELL FOR EXTERNAL COMPONENTS OF HEARING AID SYSTEMS

The present application claims the benefit of U.S. Provisional Patent Application Ser. No. 60/435,407, filed Dec. 20, 2002, which application is herein incorporated by reference in its entirety.

FIELD OF THE INVENTION

The present invention relates to hearing aid and cochlear implant systems and, more particularly, to coverings for the external components of such systems.

BACKGROUND OF THE INVENTION

Users of hearing aid and cochlear implant systems (hearing systems) have limited options to alter the appearance or function of external components for these systems. The only currently available options for altering the appearance or function of external components such as behind-the-ear sound or speech processors and headpieces are to change the color of the external components by replacing specific plastic parts of the processor or headpiece or by applying a decal to the outer surface of the processor or headpiece. Although desirable, replacing specific plastic parts is inconvenient for users. Often, users who desire to replace specific plastic parts of a processor or headpiece with a different color must request the specific color before the piece is manufactured. Then, after the new piece is manufactured and sent to the user, the original piece, which is not easily removable, can only be replaced using a tool. Even when the piece is successfully replaced, the user has only succeeded in replacing the color of the processor and has not significantly modified the overall aesthetic appearance, dimensions, shape, or function of the external components. Further, replacing plastic parts that protect the electronic circuitry of a processor can expose delicate and expensive electronic circuitry to damage.

"My days are all different, and no hour is quite like another." Helen Keller, "Dreams that Come True", as published in *Personality*, December 1927. The life of each user of a hearing system represents a unique blend of cultural, social, educational, and physical activity. This variety of activity requires a unique blend of aesthetic and functional characteristics of hearing system external components to match each user's lifestyle. Unfortunately, as mentioned above, users of hearing systems currently lack the ability to significantly, conveniently, and safely alter the external appearance and function of hearing system components. Therefore, a need exists for a system that permits users of hearings systems to significantly, conveniently, and safely alter the appearance and function of hearing system components.

SUMMARY OF THE INVENTION

The present invention addresses the above and other needs by providing a protective, interchangeable shell capable of covering a variety of separate hearing system components. The shell serves to both enhance the aesthetic appearance and protect the delicate nature of each hearing system component, thereby permitting each hearing system user to modify the user's hearing components to meet the demands of the user's unique lifestyle.

The shell adds protection. Because the shell is attached to the outer surface of the plastic component covering, it is unnecessary to remove the plastic component covering and expose delicate and expensive electronic circuitry to damage in order to change the overall color or appearance of the component. Further, an embodiment of the shell covers and protects controls that can be inadvertently changed by younger users or by active users during aggressive activity where there is no protective covering or shell on the component. The protective shell also shields the valuable component upon impact if the component falls off the user or is hit or jostled during activity. Often, hearing system users sweat during physical activity or otherwise expose their components to moisture. The protective shell serves as an added barrier that absorbs moisture or prevents moisture from penetrating the components' original casings and damaging electronic circuitry that is encased within the component's original casings.

The shell provides convenient interchangeability. The shell is conveniently and interchangeably attached to the outer surface of a Behind-the-Ear (BTE) processor, a hearing aid, a headpiece, or other hearing system component through a variety of different magnetic or mechanical attachment means, such as a simple clip-on or snap-on arrangement.

The shell improves appearance. In one embodiment, the shell is made of a disposable material so that by replacing shells, the component can maintain an overall clean and new appearance. Further, a variety of different shapes, sizes, and color schemes may be applied to the shell in a manner that makes the hearing systems more aesthetically pleasing.

The shell adds stability. The shell includes additional structure that extends around the ear or other body part to which the component attaches in order to increase the component's ability to adhere to the body. The shell can also include materials with unique characteristics that increase the shell's adherence to a user's body. This additional structure or unique material secures the component to the user better than the component could be secured alone and thus protects the component from falling off the body of a user or from unwanted movement or jostling of the component.

All of the above mentioned and other benefits of the present invention permit a hearing system user to live life unfettered by concerns of protection, usability, and appearance that previously limited the user's freedom and hampered the user's unique lifestyle.

BRIEF DESCRIPTION OF THE DRAWINGS

The above and other aspects of the present invention will be more apparent from the following more particular description thereof, presented in conjunction with the following drawings wherein.

Corresponding reference characters indicate corresponding components throughout the several views of the drawings.

DETAILED DESCRIPTION OF THE INVENTION

The following description is of the best mode presently contemplated for carrying out the invention. This description is not to be taken in a limiting sense, but is made merely for the purpose of describing the general principles of the invention. The scope of the invention should be determined with reference to the claims.

Figure 1:
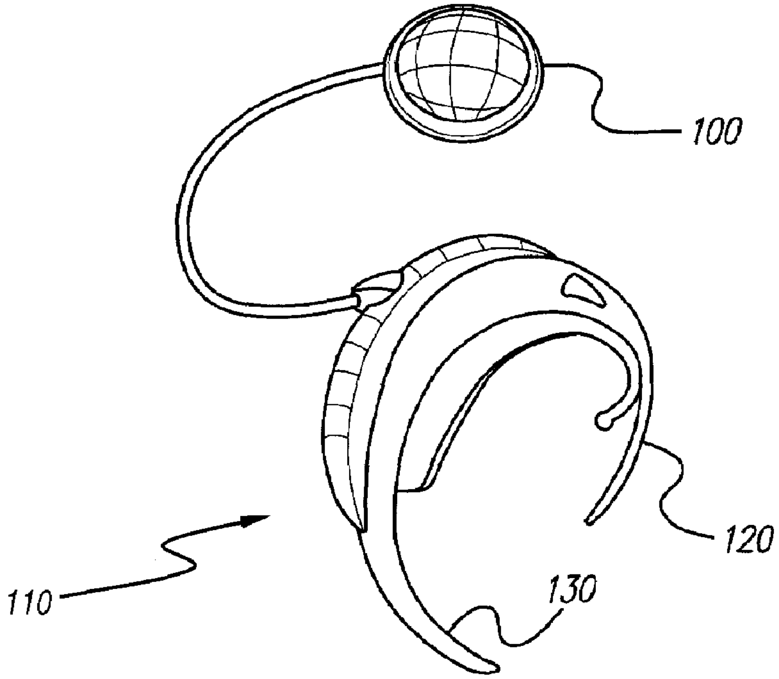
FIG. 1 is a front view of a shell system wherein a shell is attached to a headpiece and a shell is attached to a Behind-the-Ear (BTE) Unit.

FIG. 1 is a front view of a shell system wherein a headpiece shell 100 is attached to a headpiece and a shell 110 is attached to a Behind-the-Ear (BTE) Unit. Both headpiece shell 100 and shell 110 attach to external components (a headpiece and a BTE Unit) of hearing systems. Alternate embodiments of the present invention may attach to other hearing systems housing internal electronic circuitry, such as a hearing aid for amplifying ambient sounds.

Headpiece shell 100 attaches to the exterior of the headpiece and can be made of a sturdy, yet lightweight material such as plastic, rubber, or metal. The strong material of headpiece shell 100 provides added support and protection for the electronic circuitry of the headpiece from damage caused by impact or moisture. The interior of headpiece shell 100 may be formed to fit along the contours of the outside of the headpiece. A small ferrous disk may be attached to the inside of headpiece shell 100 allowing the magnetic force of the magnet inside of the headpiece to hold headpiece shell 100 onto the headpiece. Alternatively, a clip-on or snap-on attachment or any other attachment means could be used to attach shell 100 to the headpiece.

Because a simple magnetic or simple mechanical attachment means attaches headpiece shell 100 to the headpiece, no tool is required to remove and replace headpiece shell 100. Therefore, a headpiece user could easily remove and replace headpiece shell 100 with any other compatible shell to change the protective features, functions, shape, size, design, and/or overall color of the headpiece. In other words, easy interchangeability of headpiece shell 100 permits users to quickly and safely change the overall appearance and function of the BTE Unit to complement the user's current activity.

In another embodiment, headpiece shell 100 forms both the outside shell and the outer casing of the headpiece. In this embodiment, headpiece shell 100 is not as interchangeable as the previous embodiment, yet headpiece shell 100 still offers protection to the electronic circuitry of the headpiece and may be replaced using a tool.

Shell 110 may be constructed of stiff and durable materials such as plastic, hard rubber, or metal. The strong material of shell 110 provides added support and protection for the electronic circuitry of the BTE Unit from damage caused by impact or moisture. Portions of shell 110 may also be constructed of more flexible or soft materials such as soft plastic or rubber. Preferably, the portions of shell 110 that come into contact with a user's skin are covered with or made of a material that is comfortable against the skin. A material such as fabric or foam or other material with similar qualities may be used to maintain a comfortable feel against the user's skin in moist environments, such as when a user sweats.

The interior surface of shell 110 may be molded or formed to fit snugly along the contours of the back surface of a BTE Unit and may be attached to a BTE Unit through a simple mechanical attachment. For example, in one embodiment, shell 110 may be attached to the BTE Unit by sliding shell 110 onto the BTE Unit until buttons on the inside of shell 110 snap into place with corresponding holes on the BTE Unit. Easy interchangeability of shell 110 permits users to quickly and safely change the overall appearance and function of the BTE Unit to complement the user's current activity.

Shell 110 should be narrow enough to permit a user to place the tips of a pair of glasses around the pinna and next to shell 110 without feeling crowded. Further, an embodiment of shell 110 may be molded to accommodate the tips of a pair of sunglasses in a groove on an exterior surface of the shell. Further still, another embodiment of shell 110 may be molded to permit the tips of a pair of sunglasses to engage with shell 110 by snapping into a groove shaped to fit snugly with the tips.

Shell 110 covers controls on the surface of the BTE Unit in a manner that the controls cannot be manipulated when shell 110 is on the BTE Unit. This prevents unwanted manipulation of the controls while shell 110 is on the BTE Unit. An alternate embodiment of shell 110 includes an opening in the shell to allow a user to manipulate the controls of the BTE Unit. Yet another alternate embodiment of shell 110 includes corresponding control buttons and wheels in the shell to allow a user to manipulate the BTE controls through the buttons and wheels of the shell.

Shell 110 includes appendages that extend from the body of shell 110. These appendages may be an elongated nose 120 and an elongated tail 130 that wrap around the pinna of the ear. Nose 120 and tail 130 add stability to the BTE Unit on the ear and prevent the BTE Unit from falling off, moving, or jostling during aggressive activity. The weight of the battery at the bottom of the BTE Unit generates force when turning the head rapidly in either direction. This is the primary reason why the BTE Unit falls off when a user is engaged in sports. Securing the weight along the bottom of the ear reduces the centrifugal force that increases as the battery swings further from the ear.

Nose 120 and tail 130 may be constructed of a pre-molded plastic that may be formed to fit the shape of different sized ears. Alternatively, nose 120 and tail 130 may be constructed of bendable material with a bendable wire (preferably 1 mm in diameter) running through the center of nose 120 and tail

130 (see FIG. 5, wire 520) so that a user may bend and shape nose 120 and tail 130 to fit the user's unique ear shape. The bendable material is preferably a cast urethane or an injection molded thermoplastic elastomer.

Both headpiece shell 100 and shell 110 are attached to the outer surface of their respective components. Thus, by using headpiece shell 100 and shell 110, a user need not remove and replace the outer covering of the components themselves, thereby exposing the delicate and expensive electronic circuitry to damage in order to change the appearance or function of the outer covering. In essence, headpiece shell 100 and shell 110 are attachable and detachable to their respective external components of hearing systems without deconstructing or opening the external component to thereby expose internal electronic circuitry contained within the external components.

Headpiece shell 100 and shell 110 and related embodiments are not limited to fit only with BTE Units and headpieces, but may be adapted to fit any hearing system component and other consumer electronics devices small enough to be placed behind the ear such as radios, MP3 players, pagers, two-way radios and communication devices, miniature cell phones, and other after-arising technologies.

Figure 2:
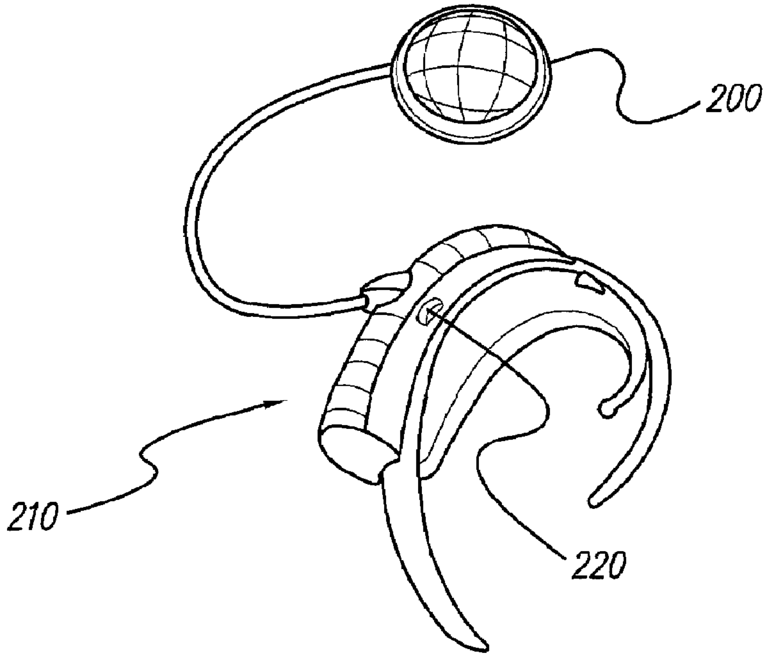
FIG. 2 is a front view of a second embodiment of a shell system wherein a shell is attached to a headpiece and a shell is attached to a BTE Unit.

FIG. 2 is a front view of a second embodiment of a shell system wherein a headpiece shell 200 may be attached to a headpiece and a shell 210 may be attached to a BTE Unit. Shell 210 includes a control wheel 220 that corresponds with a volume or other control of the BTE Unit, thus allowing a user to control the volume or other parameter of the BTE Unit with the shell 210 attached to the BTE Unit.

Figure 3:
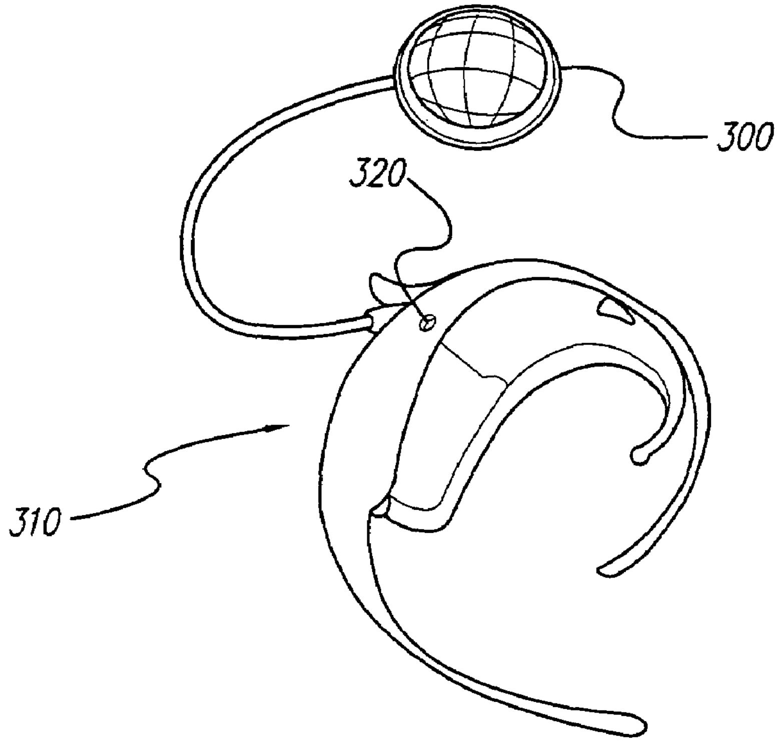
FIG. 3 is a front view of a third embodiment of a shell system wherein a shell is attached to a headpiece and a shell is attached to a BTE Unit.

FIG. 3 is a front view of a third embodiment of a shell system wherein a headpiece shell 300 may be attached to a headpiece and a shell 310 may be attached to a BTE Unit. Shell 310 includes an opening 320 that permits a user to access a control wheel or button on the BTE Unit, thus permitting the user to control at least one function of the BTE Unit with the shell 310 attached to the BTE Unit.

Figure 4:
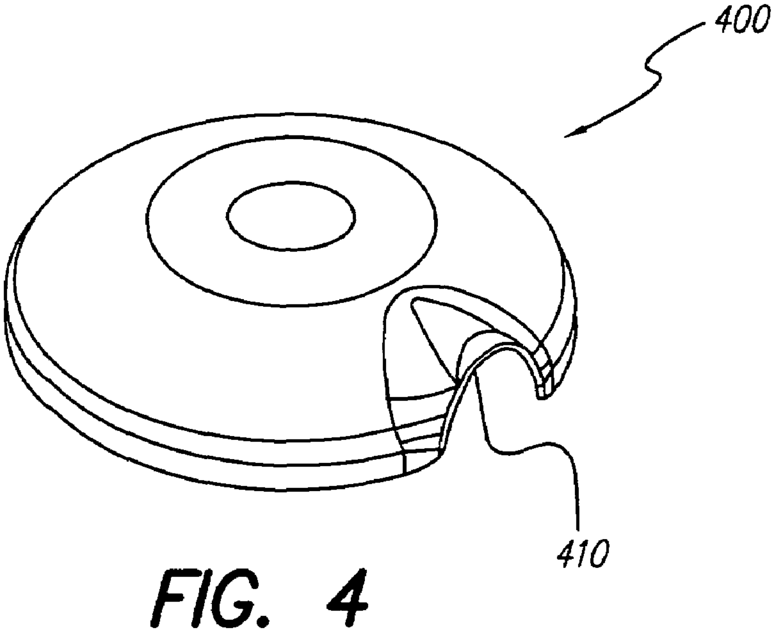
FIG. 4 is a perspective view of a fourth embodiment of a shell that attaches to a headpiece.
Figure 4A:
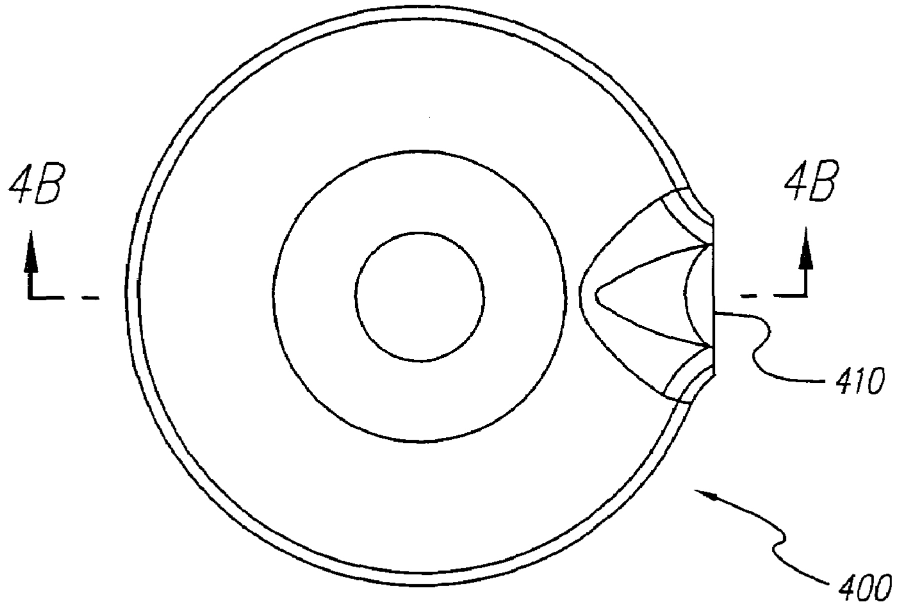
FIG. 4A is a top view of the fourth embodiment of the shell of FIG. 4.
Figure 4B:
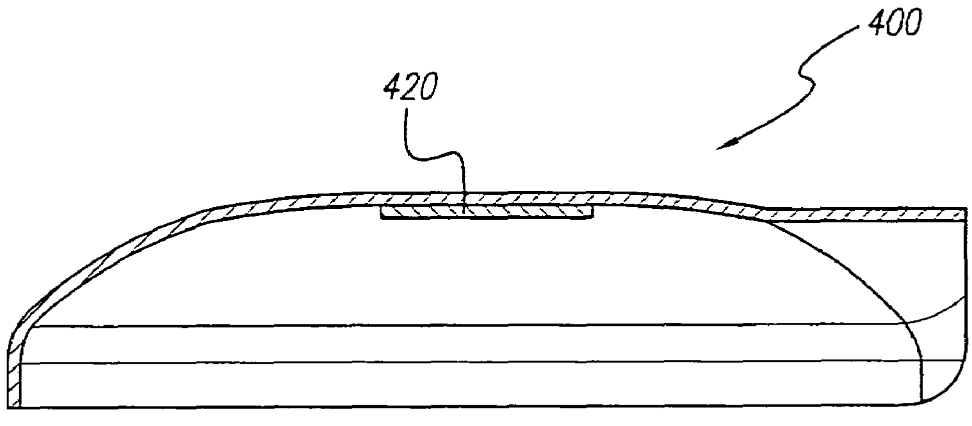
FIG. 4B is a cross-sectional view of the fourth embodiment of the shell of FIG. 4A taken along lines 4B-4B of FIG. 4A.

FIG. 4 is a perspective view of a shell 400 that attaches to a headpiece. Shell 400 may be a thin and flexible plastic membrane that may be thermally formed to fit the outside of the headpiece. The edge of shell 400 defines a hole or arch 410 that fits around a cable exiting the headpiece. FIG. 4A is a top view of shell 400. FIG. 4B is a cross-sectional view of shell 400 taken along lines 4B-4B of FIG. 4A. A small and thin ferrous disk 420, preferably constructed of nickel plated steel or any other conductive metal, may be attached to the inside of shell 400. Disk 420 may be glued to the underside of shell 400, molded into shell 400, slid into a pocket on the underside of shell 400, or attached by any other similar means.

Figure 5:
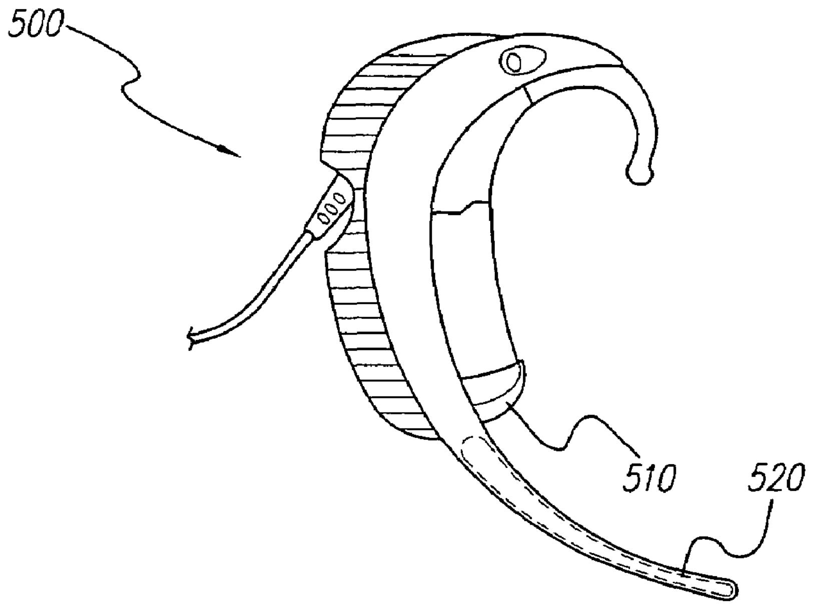
FIG. 5 is a front view of a fifth embodiment of a shell attached to a BTE Unit.

FIG. 5 is a front view of a shell 500 attached to a BTE Unit. Shell 500 differs from shell 110 (FIG. 1) in that shell 500 lacks nose 120. Further, shell 500 presents an added element of a boot 510 that attaches to the bottom, inside corner of the BTE Unit in order to strengthen the secure fit between shell 500 and the BTE Unit. All other corresponding elements, advantages, and alternate embodiments of shell 110 are a part of the design of shell 500.

Figure 6:
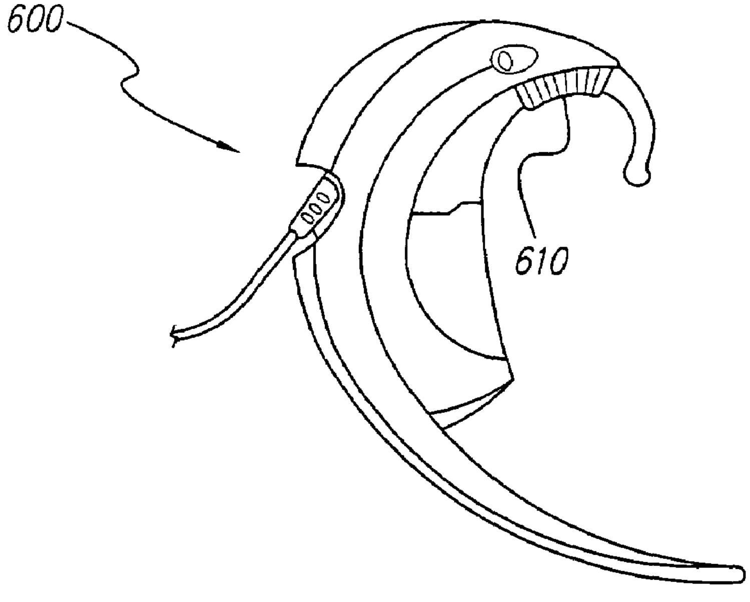
FIG. 6 is a front view of a sixth embodiment of a shell attached to a BTE Unit.

FIG. 6 is a front view of a shell 600 attached to a BTE Unit. Shell 600 differs from shell 500 (FIG. 5) in that shell 600 presents an added element of a sleeve 610 that strengthens the secure fit between the top portion of shell 600 and the ear hook of the BTE Unit. All other corresponding elements, advantages, and alternate embodiments of shell 500 are a part of the design of shell 600.

Figure 7:
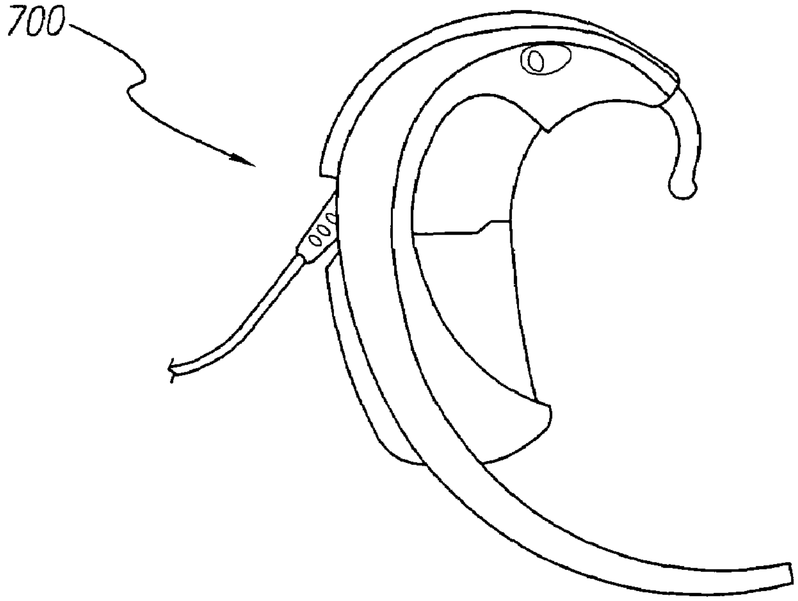
FIG. 7 is a front view of a seventh embodiment of a shell attached to a BTE Unit.

FIG. 7 is a front view of a seventh embodiment of a shell 700 attached to a BTE Unit. The embodiment of FIG. 7 is an alternate embodiment of shell 600 (FIG. 6). All corresponding elements, advantages, and alternate embodiments of shell 600 are a part of the design of the shell 700 of FIG. 7.

Figure 8:
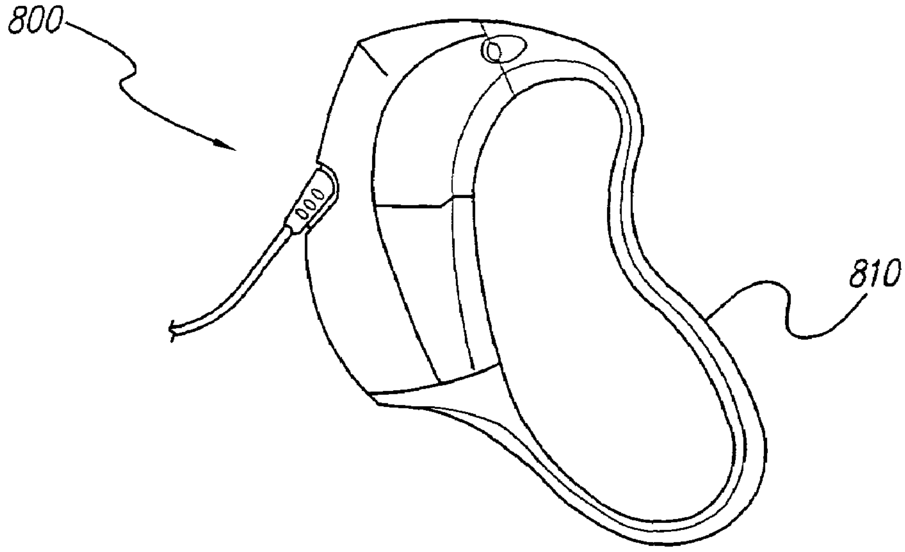
FIG. 8 is a front view of an eighth embodiment of a shell attached to a BTE Unit.

FIG. 8 is a front view of a shell 800 attached to a BTE Unit. Rather than a tail portion shown in earlier figures, the body of shell 800 includes an appendage that forms a complete ring 810 that wraps around the circumference of the ear. Like the appendages described elsewhere in this disclosure, ring 810 helps stabilize the shell 800 around the ear of a user. All other corresponding elements, advantages, and alternate embodiments of shell 600 are a part of the design of shell 800.

Figure 9:
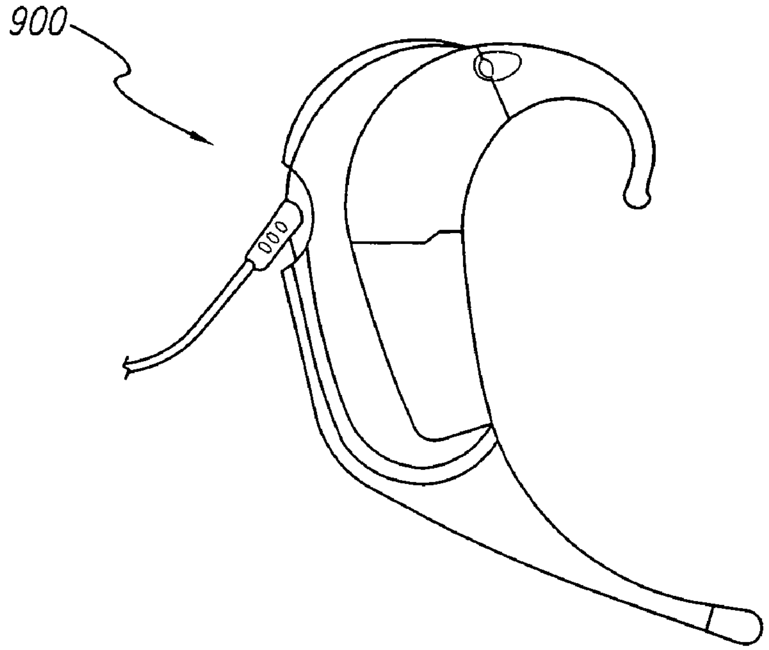
FIG. 9 is a front view of a ninth embodiment of a shell attached to a BTE Unit.

FIG. 9 is a front view of a ninth embodiment of a shell 900 attached to a BTE Unit. The embodiment of FIG. 9 is an alternate embodiment of shell 500 (FIG. 5). All corresponding elements, advantages, and alternate embodiments of shell 500 are a part of the design of the shell 900 of FIG. 9.

Figure 10:
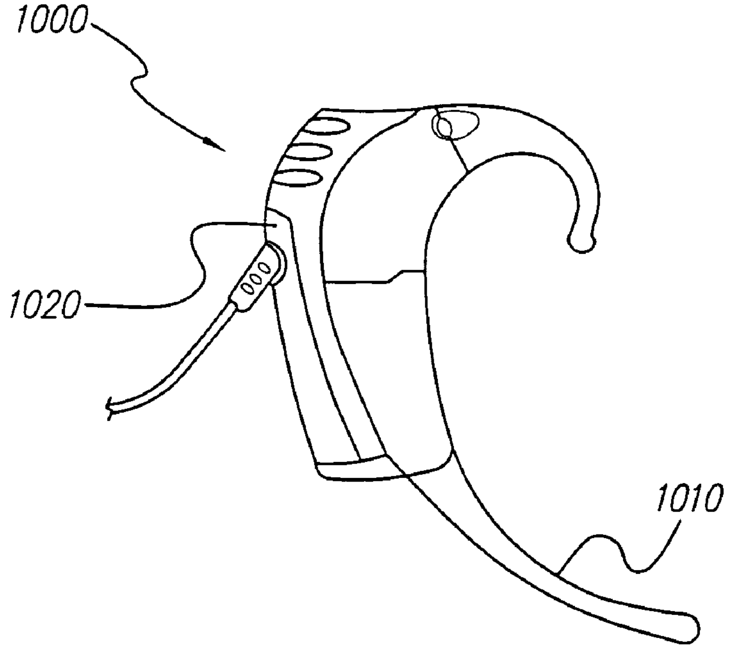
FIG. 10 is a front view of a tenth embodiment of a shell attached to a BTE Unit.

FIG. 10 is a front view of a shell 1000 attached to a BTE Unit. Shell 1000 differs from shell 110 in that shell 1000 lacks a nose 120 (FIG. 1), and a tail 1010 is not connected to a body 1020 of shell 1000 but may be rather connected directly to the base of the BTE Unit by means of a simple mechanical connection such as a snap-on or threaded arrangement. Both tail 1010 and body 1020 are attached to the BTE Unit in a manner similar to shell 110. Like the appendages described elsewhere in this disclosure, tail 1010, which is an appendage of the BTE Unit, helps stabilize the shell 1000 and BTE Unit on the ear of a user. All other corresponding elements, advantages, and alternate embodiments of shell 110 are a part of the design of shell 1000.

Figure 11:
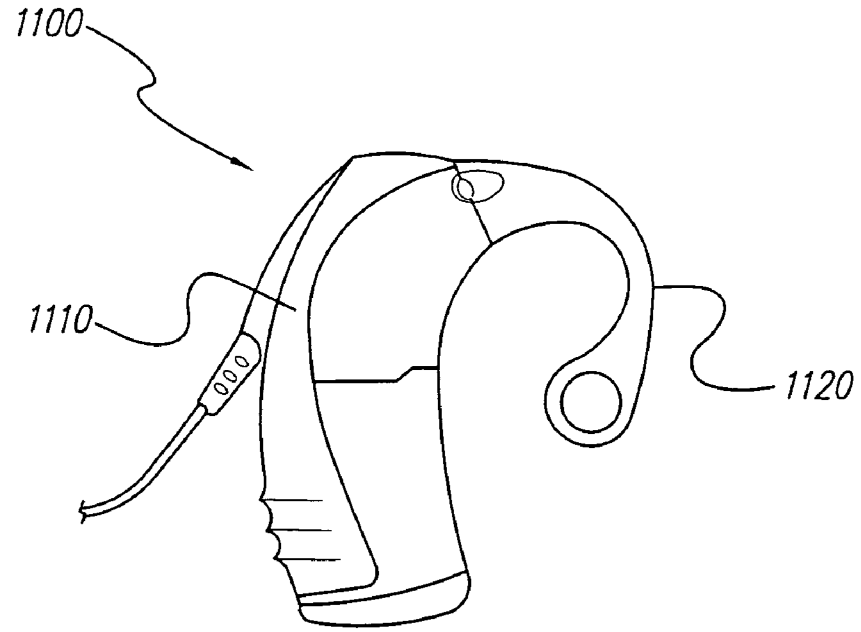
FIG. 11 is a front view of an eleventh embodiment of a shell attached to a BTE Unit.

FIG. 11 is a front view of a shell system 1100 attached to a BTE Unit. Shell system 1100 includes a body 1110 without nose or tail portions and with an elongated ear hook 1120. Elongated earhook 1120 is an appendage to the BTE Unit that may be attached by removing a normal earhook and screwing, clipping, snapping, or otherwise attaching elongated earhook 1120 to the main portion of the BTE Unit. Like the appendages described elsewhere in this disclosure, elongated earhook 1120 adds stability to the BTE Unit when worn by a user. Other than these differences noted, shell 1100 includes all other corresponding elements, advantages, and alternate embodiments of shell 110.

Figure 12:
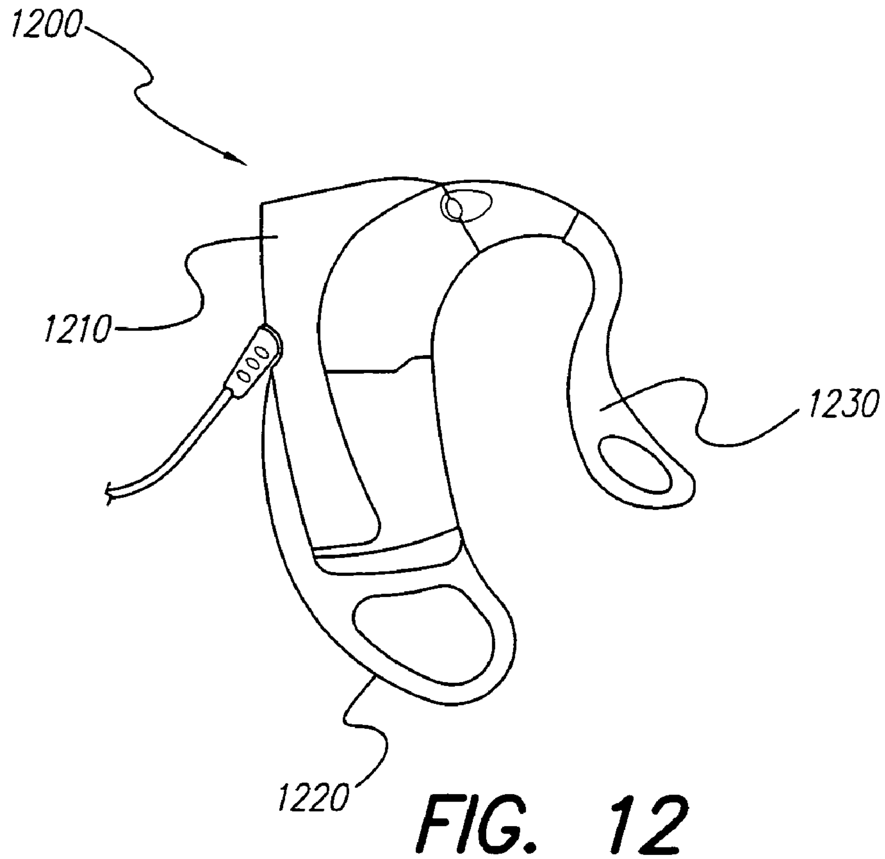
FIG. 12 is a front view of a twelfth embodiment of a shell attached to a BTE Unit.

FIG. 12 is a front view of a shell 1200 attached to a BTE Unit. Shell 1200 includes a base 1210; a hoop tail 1220 that attaches to or extends from the base of the BTE Unit and may additionally or alternately attach to or extend from base 1210; and a separate and attachable earhook extension 1230 that slides, clips, snaps, or otherwise attaches onto the end of the BTE earhook. Like the appendages described elsewhere in this disclosure, earhook extension 1230 is an appendage to the BTE Unit that helps stabilize the BTE Unit on the ear of a user. Other than these differences noted, shell 1200 includes all other corresponding elements, advantages, and alternate embodiments of shell 110.

Figure 13:
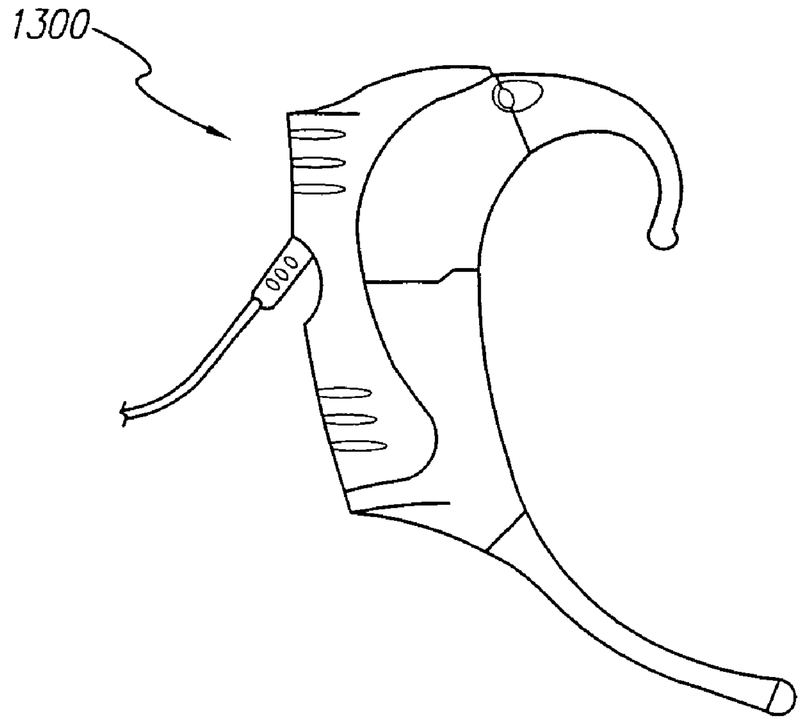
FIG. 13 is a front view of a thirteenth embodiment of a shell attached to a BTE Unit.

FIG. 13 is a front view of a thirteenth embodiment of a shell 1300 attached to a BTE Unit. The shell 1300 of FIG. 13 is an alternate embodiment of shell 1000 (FIG. 10) and includes all corresponding elements, advantages, and alternate embodiments of shell 1000.

Figure 14:
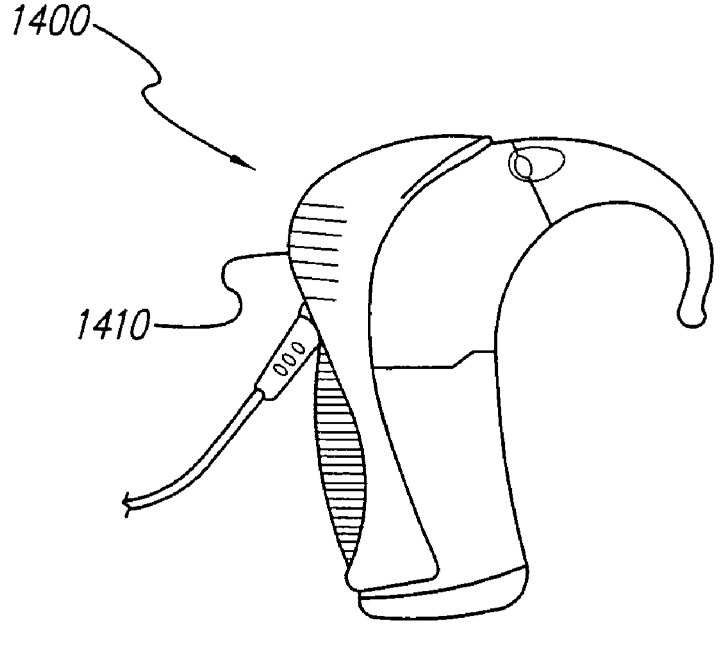
FIG. 14 is a front view of a fourteenth embodiment of a shell attached to a BTE Unit.

FIG. 14 is a front view of a shell 1400 attached to a BTE Unit. Shell 1400 includes a body 1410, but lacks a nose or tail as shown in FIG. 1. All other corresponding elements, advantages, and alternate embodiments of shell 110 are a part of the design of shell 1400.

Figure 15:
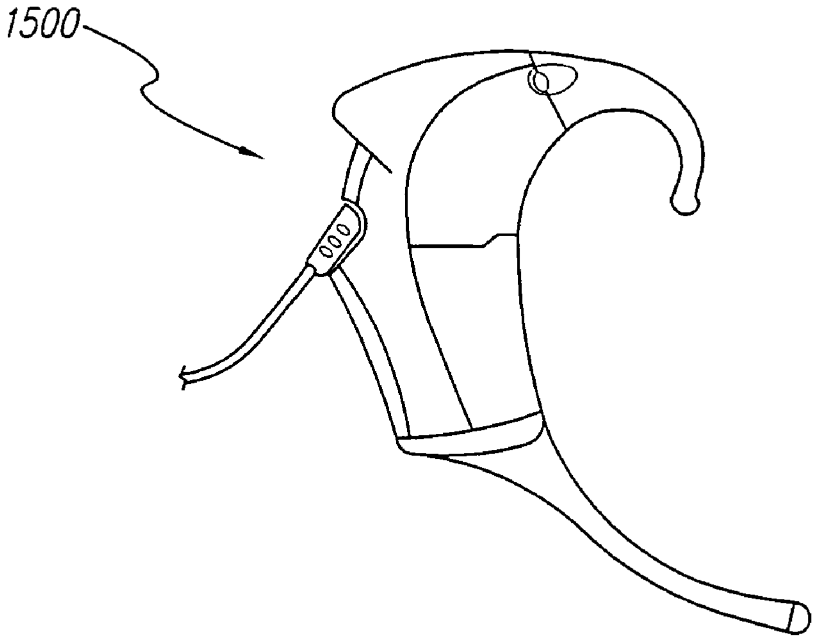
FIG. 15 is a front view of a fifteenth embodiment of a shell attached to a BTE Unit.

FIG. 15 is a front view of a fifteenth embodiment of a shell 1500 attached to a BTE Unit. The embodiment of FIG. 15 is an alternate embodiment of shell 500 (FIG. 5). All corresponding elements, advantages, and alternate embodiments of shell 500 are a part of the design of the shell 1500 of FIG. 15.

Figure 16:
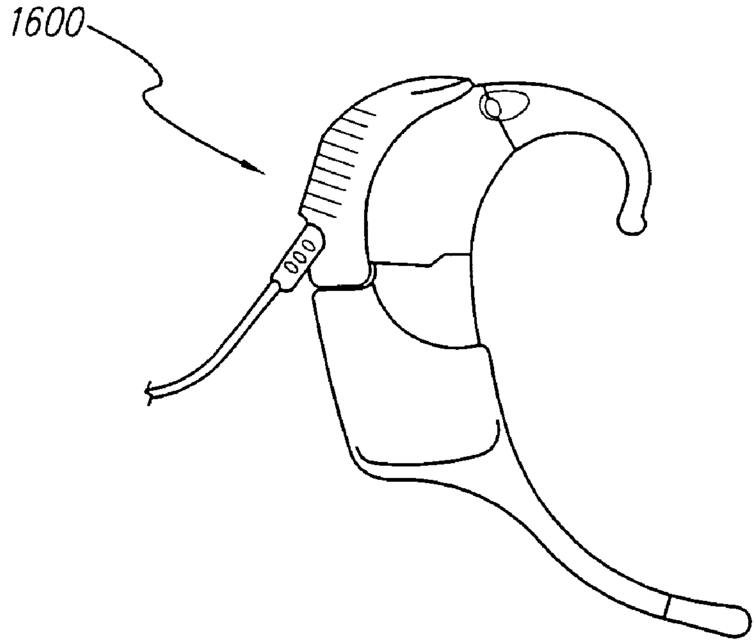
FIG. 16 is a front view of a sixteenth embodiment of a shell attached to a BTE Unit.

FIG. 16 is a front view of a sixteenth embodiment of a shell 1600 attached to a BTE Unit. The embodiment of FIG. 16 is an alternate embodiment of shell 500 (FIG. 5). All corresponding elements, advantages, and alternate embodiments of shell 500 are a part of the design of the shell 1600 of FIG. 16.

Figure 17:
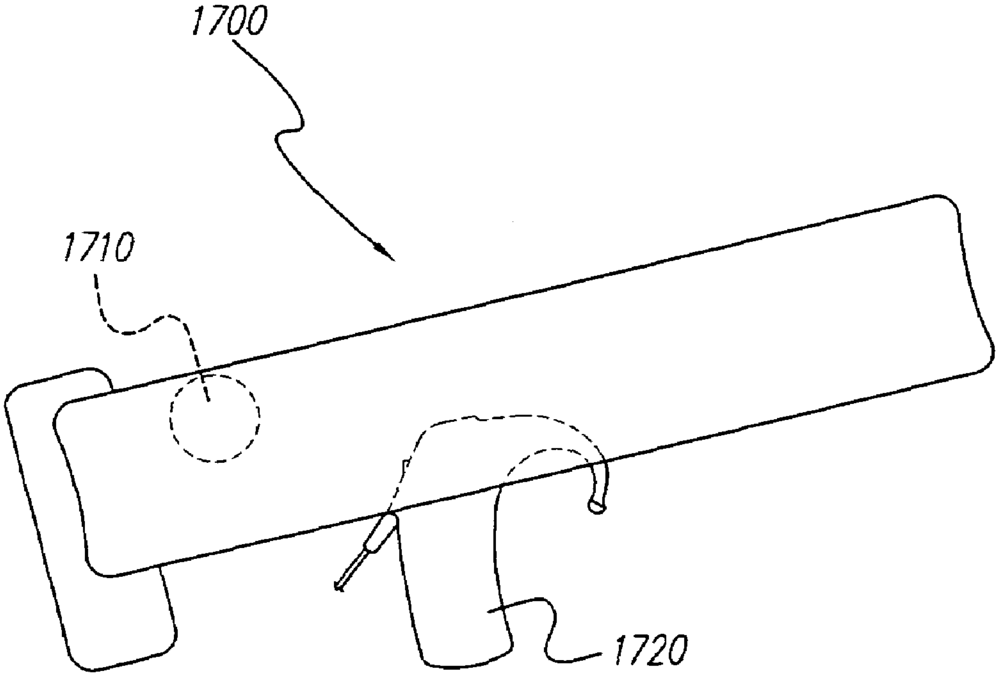
FIG. 17 is a front view of a seventeenth embodiment of a shell attached to both a headpiece and a BTE Unit.

FIG. 17 is a front view of a shell 1700 attached to both a headpiece 1710 and a BTE Unit 1720. Shell 1700 is a head band or sweat band that simultaneously secures and protects both the BTE Unit 1720 and the headpiece 1710. Shell 1700 secures the BTE Unit 1720 and the headpiece 1710 by fitting snugly over the top of them. Alternately, shell 1700 includes pockets into which the top portion of the BTE Unit 1720 and the entire headpiece 1710 may be inserted. Each pocket is shaped to fit its corresponding component.

Figure 18:
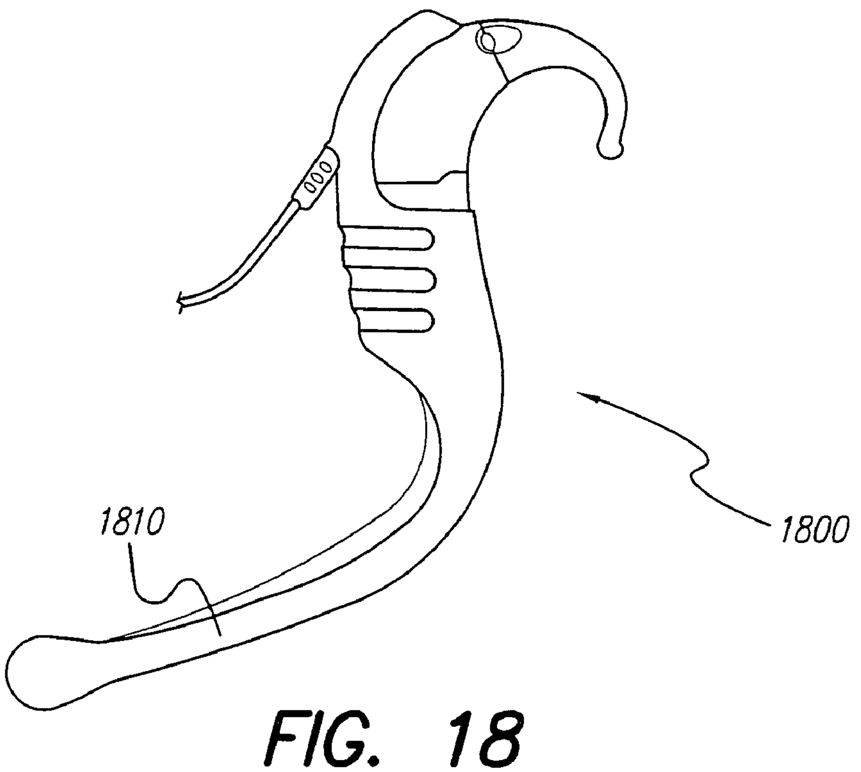
FIG. 18 is a front view of an eighteenth embodiment of a shell attached to a BTE Unit.

FIG. 18 is a front view of a shell 1800 attached to a BTE Unit. Shell 1800 includes a neckband 1810 portion combined with the features of this invention. Like other appendages described in this disclosure, neckband 1810 is an appendage to shell 1800 that increases the stability of the BTE Unit and thereby serves to prevent the BTE Unit from falling off a user's head. Shell 1800 lacks a tail and a nose but otherwise includes all other elements, advantages, and alternate embodiments of shell 110.

Figure 19:
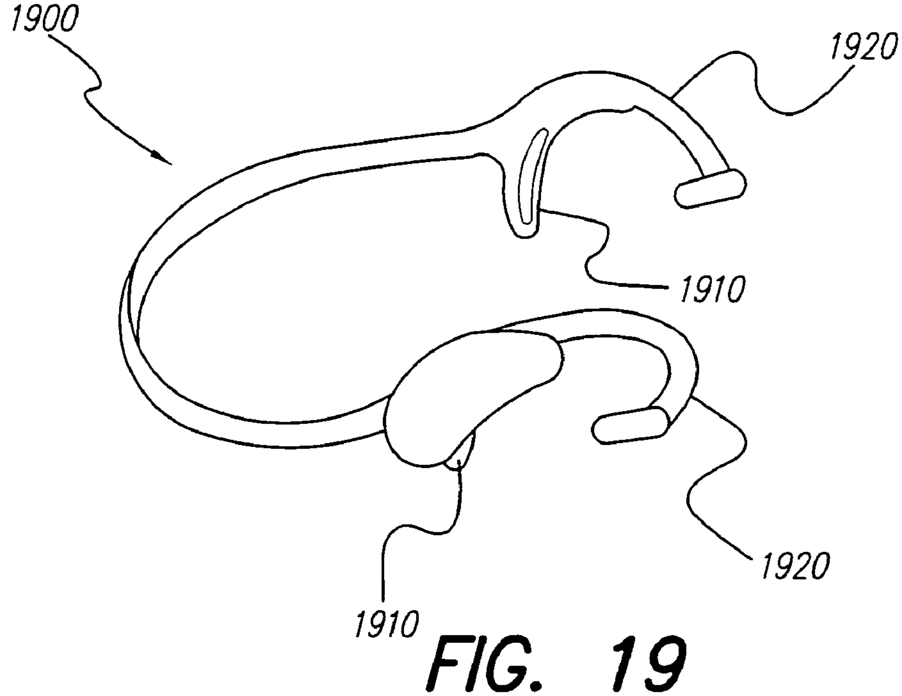
FIG. 19 is a top diagonal view of a nineteenth embodiment of a shell attached to a BTE Unit.

FIG. 19 is a top diagonal view of a shell 1900 attached to a BTE

Unit. Shell 1900 is substantially similar to shell 1800 (FIG. 18) but adds a tail 1910 and a nose 1920 at each end of shell 1900.

Figure 20:
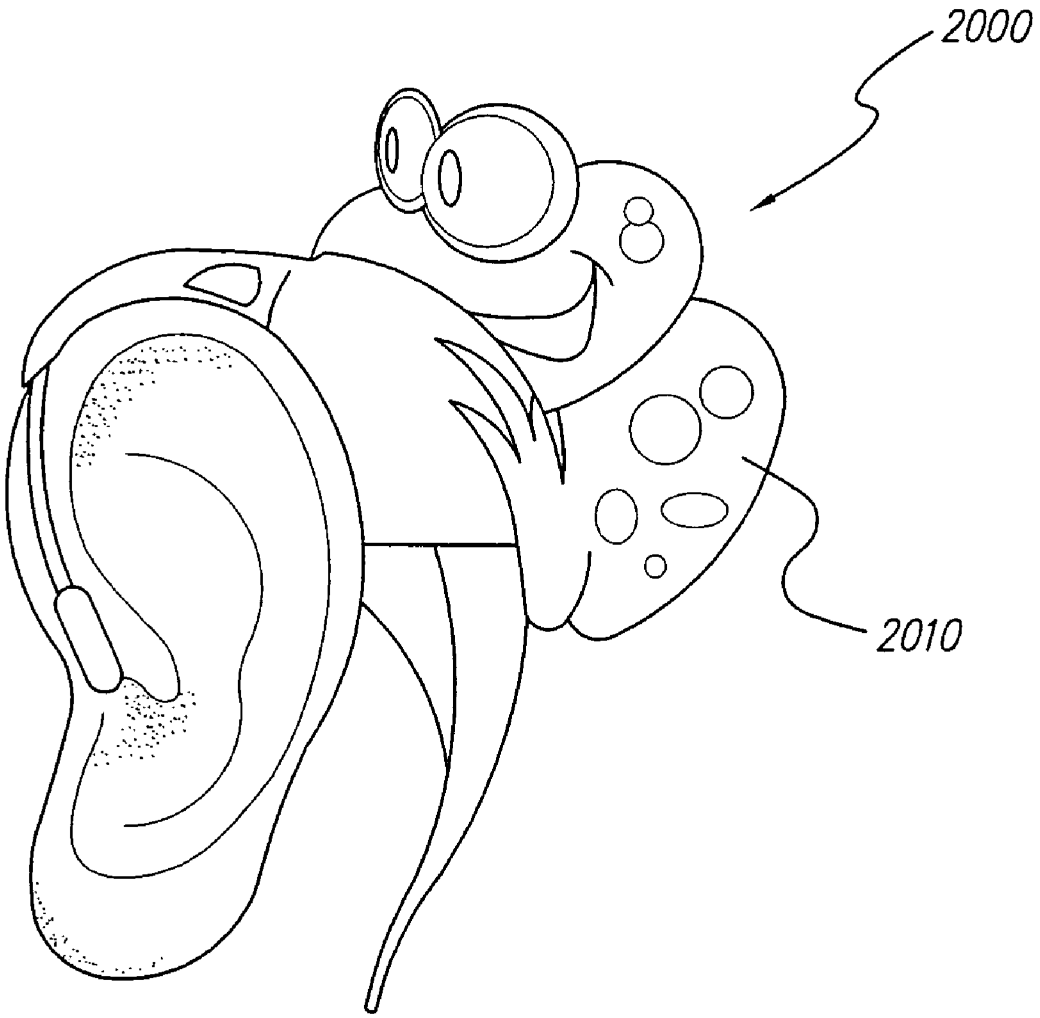
FIG. 20 is a front view of a twentieth embodiment of a shell attached to a BTE Unit.

FIG. 20 is a front view of a shell 2000 attached to a BTE Unit. Shell 2000 is designed for children and is constructed of plastic, rubber, foam, elastic fabric, or a similar material that is preferably lightweight. Plastic, rubber, foam, and thick fabric can help protect the component from scratch, moisture, or other substantial damage that is likely to occur with a young hearing system user. Shell 2000 shows a frog 2010 attached to the back portion of the BTE Unit. Alternate embodiments can include other animals, characters, or designs in different shapes, sizes, colors, and locations relative to the BTE Unit. For example, an alternate embodiment of shell 2000 includes a foam sock that slides onto the bottom portion of the BTE Unit and covers most of the BTE Unit body. Another embodiment of shell 2000 includes a sock formed of elastic fabric that slides onto the BTE Unit in a similar manner. Other embodiments of shell 2000 include foam or elastic fabric socks that cover headpieces or other hearing system components. Shell 2000 and its related embodiments can be made of disposable materials that are quickly and easily replaced in order to maintain a clean overall appearance of the hearing system components.

In summary, the present invention provides detachable shells to attach to components of a hearing system. The hearing system may be a cochlear implant system having both a behind-the-ear (BTE) external component which also includes a headpiece that is electrically connected by an electrical cord to the BTE. In the cochlear implant system, there may be a first detachable/attachable shell that covers at least part of the exterior surface of the BTE and a second, detachable/attachable headpiece shell that covers at least part of the headpiece. Alternatively, the hearing system may be a hearing aid, that amplifies ambient sounds, which hearing aid can be a behind-the-ear (BTE) device and which can be covered by a shell. Such a BTE hearing aid device, however, does not have a headpiece.

In one aspect of the invention, an attachable shell is provided for attaching to an external component of a hearing system, which shell comprises: a body with an interior surface and an exterior surface, which interior surface is formed to fit the outer surface of the external component and wherein the shell is attachable and detachable to the external component without deconstructing or opening the external component to thereby preclude exposure of internal electronic circuitry contained within the external component.

In another aspect of the invention, a hearing system is provided comprising: an external component with a housing that covers internal electronic circuitry; and a shell covering at least a part of the external component, which shell has an interior surface and an exterior surface. The shell may be attachable and detachable to the external component without deconstructing or opening the external component housing to thereby preclude exposure of internal electronic circuitry contained within the external component.

In yet another aspect of the invention, a cochlear implant system is provided comprising: an external, behind-the-ear (BTE) component with a housing that covers internal electronic circuitry; a headpiece electrically connected to the internal electronic circuitry; a first shell covering at least a part of the BTE housing; and a second, headpiece shell covering the headpiece, which headpiece shell is formed to cover at least part of the headpiece. The first shell may be attachable and detachable to the external, BTE component without deconstructing or opening the external BTE component housing to thereby preclude exposure of the internal electronic circuitry contained within the BTE component. In addition, the second, headpiece shell may be attachable and detachable to the headpiece.

In various embodiments of the invention, the first shell may include an appendage selected from the group including a nose, a tail, a hoop tail, a neckband, a ring, a nose with bendable wire along its inner diameter, a tail with bendable wire along its inner diameter, and a ring with bendable wire along its inner diameter.

The external component may be the housing of a cochlear implant BTE for directly stimulating cochlear nerves or the housing of a hearing aid BTE for amplifying ambient sounds. The external component housing of either type of devices can include an appendage selected from the group including a nose, a tail, a hoop tail, a neckband, a ring, a nose with bendable wire along its inner diameter, a tail with bendable wire along its inner diameter, and a ring with bendable wire along its inner diameter.

The exterior surface of the first shell may include a groove shaped to accommodate the tips of a pair of glasses. Further, the exterior surface of the first shell may include at least one tactile control, which at least one control can manipulate at least one corresponding control along the surface of an external component, e.g., the cochlear implant BTE or the hearing aid BTE.

While the invention herein disclosed has been described by means of specific embodiments and applications thereof, numerous modifications and variations could be made thereto by those skilled in the art without departing from the scope of the invention set forth in the claims.

What is claimed is:

1. A cochlear implant system comprising:

an external behind-the-ear (BTE) component including a housing and internal electronic circuitry in said housing;

a headpiece separate from the BTE and electrically connected to the internal electronic circuitry;

a first shell covering at least a part of the BTE housing; and a second shell covering the headpiece, wherein the headpiece shell is formed to cover at least part of the headpiece;

wherein the first shell is attachable and detachable to the external, BTE component without deconstructing or opening the external BTE component housing to thereby preclude exposure of the internal electronic circuitry contained within the BTE component;

wherein the second, headpiece shell is attachable and detachable to the headpiece, and wherein the headpiece shell further includes an attachable sleeve placed on a top portion of the headpiece shell.

2. A cochlear implant system comprising:

an external behind-the-ear (BTE) component including a housing and internal electronic circuitry in said housing;

a headpiece separate from the BTE and electrically connected to the internal electronic circuitry;

a first shell covering at least a part of the BTE housing; and a second shell covering the headpiece, wherein the headpiece shell is formed to cover at least part of the headpiece;

wherein the first shell is attachable and detachable to the external, BTE component without deconstructing or opening the external BTE component housing to thereby preclude exposure of the internal electronic circuitry contained within the BTE component;

wherein the second, headpiece shell is attachable and detachable to the headpiece, wherein the BTE component housing includes an ear hook; and wherein the first shell further includes an earhook extension that is attachable to the ear hook.

3. The cochlear implant system of claim 2, further comprising an electrical cord wherein the headpiece is electrically connected by the electrical cord to the internal electronic circuitry.

4. The cochlear implant system of claim 2, wherein the first shell comprises one or more materials selected from the group consisting of: plastic, rubber, metal, fabric, and foam.

5. The cochlear implant system of claim 2, wherein the first shell is configured to prevent moisture from penetrating the BTE housing.

6. The cochlear implant system of claim 2, further comprising a clip-on or snap-on arrangement wherein at least one of the first shell and the headpiece shell is attachable using the clip-on or snap-on arrangement.

7. A cochlear implant system comprising:

an external behind-the-ear (BTE) component including a housing and internal electronic circuitry in said housing;

a headpiece separate from the BTE and electrically connected to the internal electronic circuitry;

a first shell covering at least a part of the BTE housing; and a second shell covering the headpiece, wherein the headpiece shell is formed to cover at least part of the headpiece;

wherein the first shell is attachable and detachable to the external, BTE component without deconstructing or opening the external BTE component housing to thereby preclude exposure of the internal electronic circuitry contained within the BTE component;

wherein the second, headpiece shell is attachable and detachable to the headpiece, wherein the first shell comprises buttons, wherein the BTE component comprises holes for engagement with the buttons, and wherein the first shell is attachable to the BTE component by sliding the first shell onto the BTE component until the buttons engage with the holes.

8. The cochlear implant system of claim 7, further comprising an electrical cord wherein the headpiece is electrically connected by the electrical cord to the internal electronic circuitry.

9. The cochlear implant system of claim 7, wherein the BTE component further comprises controls, and the first shell protects the controls from being inadvertently changed.

10. The cochlear implant system of claim 7, wherein the BTE component further comprises controls, and the first shell allows access to the controls.

11. The cochlear implant system of claim 7, wherein the BTE component further comprises controls, the first shell further comprises shell controls corresponding to the BTE component controls, wherein the shell controls allow a user to manipulate the BTE component controls.

12. The cochlear implant system of claim 7, wherein the first shell comprises one or more materials selected from the group consisting of: plastic, rubber, metal, fabric, and foam.

13. The cochlear implant system of claim 7, wherein the first shell is configured to prevent moisture from penetrating the BTE housing.

14. The cochlear implant system of claim 7, wherein the BTE component housing includes an appendage selected from the group consisting of a nose, a tail, a hoop tail, an earhook extension, a ring, a nose with bendable wire along its inner diameter, a tail with bendable wire along its inner diameter, and a ring with bendable wire along its inner diameter.

15. The cochlear implant system of claim 7, wherein the first shell includes an appendage that helps stabilize the first shell around the ear of a user.

16. The cochlear implant system of claim 7, wherein the first shell includes an appendage selected from the group consisting of a nose, a tail, a hoop tail, a neckband, a ring, a nose with bendable wire along its inner diameter, a tail with bendable wire along its inner diameter, and a ring with bendable wire along its inner diameter.

17. The cochlear implant system of claim 7, wherein the first shell comprises a groove on an exterior surface of the shell configured to accommodate a pair of glasses.

18. The cochlear implant system of claim 7, wherein the headpiece shell comprises one or more materials selected from the group consisting of: plastic, rubber, and metal.

19. The cochlear implant system of claim 7, wherein the headpiece shell is made from a flexible plastic.

20. The cochlear implant system of claim 7, wherein the headpiece shell further comprises a ferrous disk, wherein the ferrous disk is magnetically attracted to a magnet placed within the headpiece to thereby facilitate attachably holding the headpiece shell firmly against the headpiece, while permitting the headpiece shell to be detachable from the headpiece.

* * * * *